United States Patent [19]

Gammons et al.

[11] 4,149,541

[45] Apr. 17, 1979

[54] FLUID CIRCULATING PAD

[75] Inventors: Clifford E. Gammons; Francis C. Moore; Leon R. Perkinson, all of Indianapolis, Ind.

[73] Assignee: Moore-Perk Corporation, Indianapolis, Ind.

[21] Appl. No.: 841,361

[22] Filed: Oct. 6, 1977

[51] Int. Cl.² ............................................. A61F 7/00
[52] U.S. Cl. ..................................... 128/400; 128/402
[58] Field of Search ............... 128/400, 402, DIG. 20, 128/149, 254, 399, 64, 33, 24.1, 24 R, 82.1, 87 R; 5/349, 350

[56] References Cited

U.S. PATENT DOCUMENTS

| | | | |
|---|---|---|---|
| 396,208 | 1/1889 | Herndon | 128/400 |
| 735,876 | 8/1903 | Holland | 128/258 |
| 1,902,016 | 3/1933 | Copeland | 128/400 |
| 3,199,124 | 8/1965 | Grant | 5/349 |
| 3,462,778 | 8/1968 | Whitney | 5/347 |
| 3,468,311 | 9/1969 | Gallagher | 5/350 X |
| 3,717,145 | 2/1973 | Berndt et al. | 128/82.1 |
| 3,867,939 | 2/1975 | Moore et al. | 128/254 |
| 3,871,381 | 3/1975 | Roslonski | 128/400 |
| 3,894,213 | 7/1975 | Agarwala | 219/297 |
| 3,995,621 | 12/1976 | Fletcher et al. | 128/2 H |

OTHER PUBLICATIONS

Gaymar-New Product Release on T-Pad, Nov. 15, 1976.

*Primary Examiner*—Lawrence W. Trapp
*Attorney, Agent, or Firm*—Larry N. Barger

[57] ABSTRACT

A flexible pad with interconnecting internal passages for circulating a hot or cold liquid for treating a patient. The pad has an improved internal flow pattern that includes a set of partitions that separate the pad into a plurality of major fields that are connected in series to insure that liquid flows to all areas, i.e. fields, of the pad even when such pad is in folded condition. Within each field is a series of passages forming a crisscross waffle grid pattern for random liquid flow in many directions within each field to reduce the chance of blocking liquid circulation through the pad when it is in folded condition.

20 Claims, 5 Drawing Figures

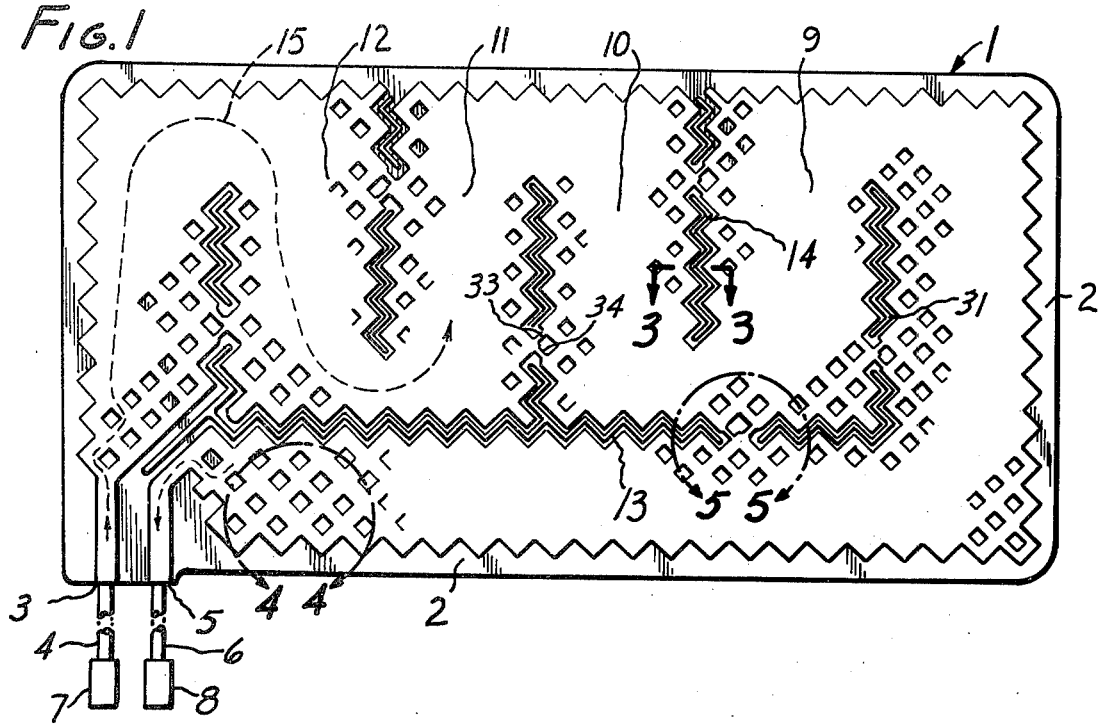
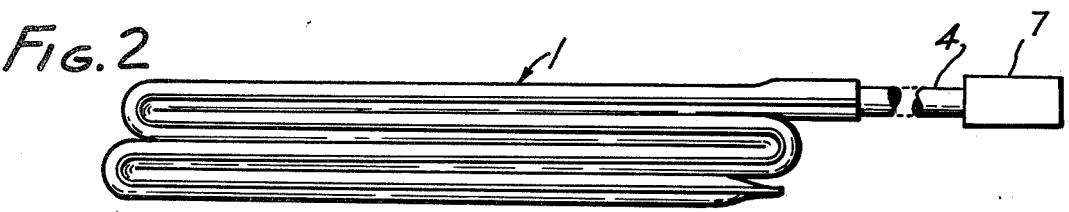
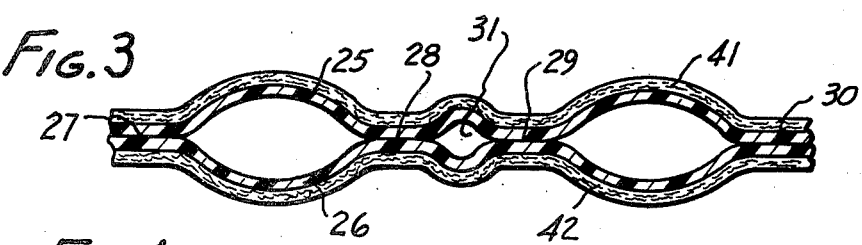
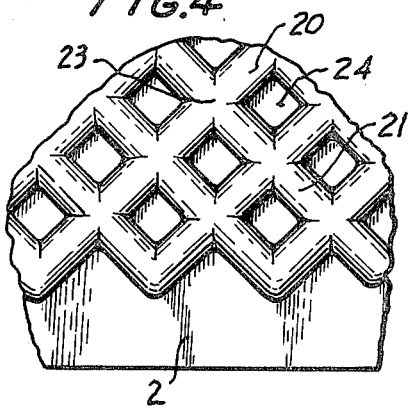
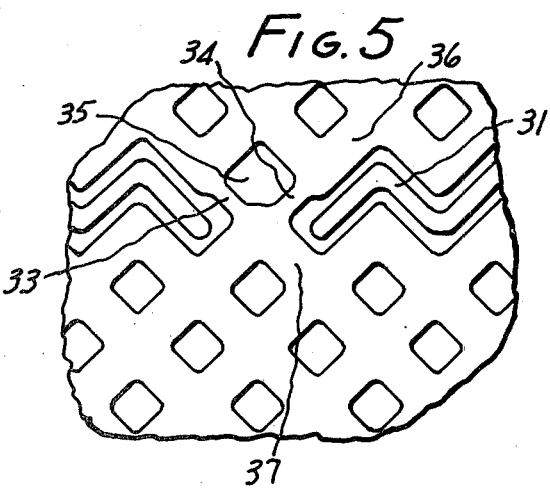

FLUID CIRCULATING PAD

BACKGROUND OF THE INVENTION

It is well-known to treat portions of the human body with a hot or cold compress to aid in healing muscle injury, surgical wounds, etc. One very convenient way of applying such a compress is with a flexible pad with interconnecting passages through which is circulated a hot or cold fluid, usually water, by means of a small pump. Temperature of the fluid is controlled by a heater in the pump, or with refrigeration or an ice bath external of the patient contact pad.

Because of the wide variation of curves, angles, etc. of the human anatomy, it is common practice to fold the fluid circulating pad to provide a more precise contour and size of the pad against a particular portion of the patient's body. For instance, applying a flat pad to an elbow or ankle area usually requires some bending or folding of the pad. In hospitals, it is also common practice to fold the pad as one might fold a blanket simply to reduce its size to ¼ or so of its normal unfolded size.

Such folding has created problems in flexible fluid circulating pads because often the fold causes a crimp in the fluid circulating passages, which stops or slows down the circulation through the pad. This can seriously affect the maintenance of a constant temperature to the patient, i.e. hot or cold. Liquid circulates better through a folded patient treatment pad when the liquid can flow randomly in several different directions. Thus, if one small area of the pad has a particularly tight crimp, the liquid seeks the passage of least resistance and can detour around the particular flow restricting crimp. Random interconnecting flow patterns are shown in FIG. 2 of the Herndon U.S. Pat. No. 396,208 and Holland U.S. Pat. No. 735,876.

A patient treatment pad has been proposed, the Gaymar T-pad, which includes a series of round "button" seals that provide a random passage between the buttons over generally the entire patient contact area of the pad. A narrow inlet channel along one edge of the pad and a narrow outlet channel along another edge of the pad is provided by a row of buttons more closely spaced together than the remaining buttons of the pad. Except for the narrow inlet and outlet channels, the entire pad has a random circulation pattern around the round buttons.

The above types of random fluid flow pads would help reduce the flow restriction caused by folding the pad. However, this same round button pattern over substantially the entire patient treatment area of the pad causes liquid to take the path of least resistance in a folded pad, and certain areas of the pad would have little or no circulation. For instance, if an inlet were at one corner of a rectangular pad and an outlet at a diagonally opposite corner, most flow would occur between the diagonally opposite inlet and outlet and the other two corner areas would have much slower circulation, if any. This uneven circulation would cause temperature variations throughout the pad.

SUMMARY OF THE INVENTION

This invention overcomes the above problems by providing a fluid circulation pad that is separated into several major fields by internal partitions which preferably are connected in series between an inlet and outlet of the pad so that fluid is forced to flow through all fields of the pad. Within each field is a crisscross waffle pattern of interconnected passages with each passage having portions with generally parallel sides to provide pronounced zigzag motion to fluid flow. Thus, as the pad is folded, the partitions force the fluid to flow through all of the fields, without taking a shortcut through a path of least resistance through only a small portion of the pad. Once within a field, fluid is free to flow in a variety of directions for detouring around any severely crimped area of the pad.

THE DRAWINGS

FIG. 1 is a top plan view of the fluid circulating pad shown in unfolded condition;

FIG. 2 is an enlarged end view of the pad of FIG. 1 showing it in folded condition;

FIG. 3 is an enlarged sectional view taken along line 3—3 of a partition;

FIG. 4 is an enlarged fragmentary view of FIG. 1 showing the waffle grid pattern; and FIG. 5 is an enlarged fragmentary view of a portion of FIG. 1 showing the narrow bleed passages between adjoining partitioned fields of the pad.

DETAILED DESCRIPTION

FIG. 1 shows a patient treatment pad 1 which is formed by a pair of flexible thermoplastic panels sealed together about a peripheral seal 2 to define a sealed internal chamber with an inlet port 3 connected to an inlet tube 4. An outlet port 5 is sealed to an outlet tube 6. Inlet tube 4 and outlet tube 6 have connectors 7 and 8 connected to their respective ends. A circulating pump (not shown) can join to connectors 7 and 8.

The fluid circulating pad is segregated into a series of fields 9, 10, 11 and 12 by partitions such as 13 and 14. It is preferable to have the major fields connected in series, such as in serpentine fashion as shown in FIG. 1. Thus as liquid enters inlet tube 4, it is forced to flow in a serpentine manner as shown by dotted line 15. In this manner liquid is forced to all areas of the pads to maintain proper temperature control of the entire pad area. In the pads it is desirable to include four or more separate fields, none of which occupies more than ½ of the pad's treatment area.

Within each partitioned field of the pad are a series of intersecting passages with portions having generally parallel sides to create a waffle like grid pattern with rectangular or diamond shaped sealed portions between the passages. In the enlarged section of FIG. 4, the passages are indicated as 20 and 21 that intersect at 23. A rectangular sealed section 24 seals the two thermoplastic panels of the pad together. Such rectangular seal provides generally parallel sides to the passage that provides a more pronounced zigzag path for the fluid than a pad sealed with round buttons as the Gaymar T-pad.

The waffle grid pattern allows the circulating liquid to flow in several different directions. Thus, if a crease in the folded pad should block off one particular passage, such as 20, liquid can detour around crimped passage 20 and still flow through the serpentine series connected fields. Thus, the partitioning system between the fields provide major directional guidance for the liquid, while the waffle grid pattern within each field provides a random circulation within the field as liquid flows from an inlet of the field to an outlet of the field.

FIG. 3 is an enlarged sectional view taken along line 3—3 of FIG. 1 showing the seal construction at the partition system. Here an upper thermoplastic panel 25 overlies a bottom thermoplastic panel 26. These two panels are sealed together at 27, 28, 29 and 30. Preferably, there is a small gap 31 between seals 28 and 29. Gap 31 is sealed at its ends and does not provide a liquid passage. Its purpose is merely to separate field 28 and 29 to give a "double seal" of two closely spaced seams at the partition. Such double seals can be in a zigzag fashion as shown in FIG. 1. The double seals at the partitions provide for improved reliability. For instance, if seal 28 should rupture, seal 29 will still keep the partition intact.

FIG. 5 shows a pair of transverse tiny bleed passages 33 and 34 that extend across a partition 35 to connect a portion of a waffle grid pattern 36 in one field with a waffle grid pattern of an adjoining field. As shown in FIG. 5, the small passage 31 separating the double seals of the partition has been closed at its end. A partition at area 35 has a single wider field that is roughly equivalent in width to the combined double seals of the remaining portions of the partition.

The purpose of the narrow bleed passages 33 and 34 is to prevent a pressure buildup in one particular field if the pad is folded in a very crimped and tight manner to block off an exit passage from a particular field. However, the bleed passages 33 and 34 are sufficiently small so that they do not interfere with the normal control of liquid flow through the serpentine passage under normal operation of the pad when in folded condition.

It is preferable to have a fabric, such as a nonwoven absorptive material 41 sealed to at least one side of the pad as shown in FIG. 3. Preferably a second fabric covering 42 is sealed to an opposite side of the pad. Preferably the fabric coverings are sealed in a pattern that is identical to that used to seal the two thermoplastic panels together. One covering can carry a notation for use in moist therapy wherein the fabric is dampened, and the opposite fabric covering can be labelled and used for dry therapy. The details of connecting the fabric covering to the thermoplastic panels is described in our co-pending application entitled Patient Treatment Pad for Hot or Cold Use, filed Mar. 2, 1977, Ser. No. 773,673 now U.S. Pat. 4,114,620.

The fluid circulating pads of this invention with the partitioning system and waffle grid structure can be of any size, even up to full bed sheet size. However, a typical size might be 1 ft.×1.5 ft. This size would have both the field partition and waffle grid structure. In very small sizes, such as a neck collar treating pad of approximately 2-3 inch width, which is not normally folded, only the waffle grid pattern need be used.

In the foregoing description, a specific example has been used to illustrate the invention. However, those skilled in the art will understand how to make certain modifications to this example without departing from the spirit and scope of the invention.

We claim:

1. A fluid circulating pad with a pair of panels sealed together to define flow passages therebetween, wherein the improvement comprises: a plurality of interconnected fields in the pad separated by partitions; and within each field are a series of passages with portions having generally parallel sides and there is one or more crisscross intersections between passages within such field.

2. A fluid circulating pad as set forth in claim 1, wherein the fields are arranged in a generally serpentine arrangement.

3. A fluid circulating pad as set forth in claim 1, wherein the passages within the fields are interconnected in a crisscross arrangement in a waffle grid pattern.

4. A fluid circulating pad as set forth in claim 1, wherein the partition between the fields have one or more bleed passages therethrough.

5. A fluid circulating pad as set forth in claim 1, wherein the pad is flexible and capable of being folded without substantial blockage of circulating fluid flow through the pad.

6. A flexible foldable fluid circulating pad with a pair of panels sealed together at spaced locations to define therebetween a series of passages having portions with generally parallel sides and these passages are interconnected in a waffle grid pattern.

7. A pad as set forth in claim 6, wherein the waffle grid pattern is segregated into a plurality of interconnected fields by partitions.

8. A pad as set forth in claim 7, wherein the fields are arranged in series, so that fluid flows sequentially through the fields.

9. A pad as set forth in claim 6, wherein the panels include two flexible thermoplastic panels sealed together; and a liquid absorptive fabric panel sealed to an outer surface of at least one thermoplastic panel in the same waffle grid pattern as sealed together the two thermoplastic panels.

10. A pad as set forth in claim 9, wherein both thermoplastic panels have fabric outer panels sealed to their outer surface in the same waffle grid pattern, and at least one of the fabric panels is liquid absorptive.

11. A flexible foldable patient treatment pad for circulating a fluid therebetween, while in a folded condition comprising: a pair of flexible thermoplastic panels sealed together in a pattern to define four or more interconnected fields separated by partitions; and a series of crisscross interconnected passages within each field.

12. A pad as set forth in claim 11, wherein the fields are connected in series, so that fluid flows sequentially through the fields.

13. A pad as set forth in claim 12, wherein the fields are arranged in a serpentine configuration.

14. A pad as set forth in claim 11, wherein the partitions have one or more bleed passages therethrough.

15. A pad as set forth in claim 14, wherein the bleed passages are substantially narrower than the internal passages within the fields.

16. A pad as set forth in claim 11, wherein the series of interconnected passages are formed by a series of sealed areas between the thermoplastic panels, and the sealed areas have parallel and planar sides.

17. A pad as set forth in claim 16, wherein each sealed area is of a generally rectangular shape.

18. A flexible foldable fluid circulating pad having a pair of panels sealed together at spaced locations to define a plurality of fields connected in series, and none of these fields occupies more than ½ of the pad's circulating area, for insuring fluid flow to all fields even when the pad is folded; and a plurality of intersecting passages within each field, said passages having a pattern that permits random nonparallel flow through each field, thereby reducing the chance of fluid flow stoppage through the pad when in folded condition.

19. A pad as set forth in claim 18, wherein the fields are arranged in serpentine configuration.

20. A flexible foldable patient treatment pad for circulating a fluid therein while in a folded condition comprising: a pair of flexible thermoplastic panels sealed together about their periphery, and defining an inlet port and an outlet port at their edges; a tubular fluid inlet tube connected to the inlet port; a tubular fluid outlet tube connected to the outlet port; connecting adapters on the outer ends of the inlet and outlet tubes; said thermoplastic panels having an interior segregated into four or more fields connected in series in a serpentine configuration by partition seals between the two thermoplastic panels; a series of interconnected passages within each field forming a crisscross waffle pattern, said passages being separated by a series of sealed sections having planar generally parallel surfaces; and a liquid absorptive fabric panel secured to an outer surface of one thermoplastic panel in a pattern that is superimposed and substantially identical with the pattern sealed between the two thermoplastic panels, whereby liquid can flow between the inlet and outlet tubes while in a folded condition and press against a patient without substantially blocking liquid flow through the pad.

* * * * *